(12) United States Patent
Tanaka et al.

(10) Patent No.: US 9,389,202 B2
(45) Date of Patent: Jul. 12, 2016

(54) DAMAGE DETECTING DEVICE FOR SUPPORTING STRUCTURE FOR ARMATURE SHAFT

(71) Applicant: CENTRAL JAPAN RAILWAY COMPANY, Aichi (JP)

(72) Inventors: Mamoru Tanaka, Aichi (JP); Masayuki Ueno, Aichi (JP); Yoshiya Watanabe, Aichi (JP); Hirokazu Kato, Aichi (JP)

(73) Assignee: CENTRAL JAPAN RAILWAY COMPANY, Aichi (JP)

( * ) Notice: Subject to any disclaimer, the term of this patent is extended or adjusted under 35 U.S.C. 154(b) by 0 days.

(21) Appl. No.: 14/420,321

(22) PCT Filed: Aug. 8, 2013

(86) PCT No.: PCT/JP2013/071523
§ 371 (c)(1),
(2) Date: Feb. 6, 2015

(87) PCT Pub. No.: WO2014/024979
PCT Pub. Date: Feb. 13, 2014

(65) Prior Publication Data
US 2015/0204818 A1 Jul. 23, 2015

(30) Foreign Application Priority Data

Aug. 8, 2012 (JP) ................................ 2012-176300

(51) Int. Cl.
*G01N 27/82* (2006.01)
*G01B 7/30* (2006.01)
(Continued)

(52) U.S. Cl.
CPC .............. *G01N 27/82* (2013.01); *B60L 3/0023* (2013.01); *B60W 10/08* (2013.01); *H02K 7/14* (2013.01);
(Continued)

(58) Field of Classification Search
CPC ...................................................... G01N 27/82
USPC ........................................................ 324/240
See application file for complete search history.

(56) References Cited

U.S. PATENT DOCUMENTS 4,439,730 A * 3/1984 Kauffman ...................... 324/232
2003/0006760 A1 * 1/2003 Valles ....................... 324/207.15
(Continued)

FOREIGN PATENT DOCUMENTS

JP 4-5525 A 1/1992
JP 4-32724 A 2/1992
(Continued)

OTHER PUBLICATIONS

Form PCT/ISA/210 (International Search Report) for PCT/JP2013/071523 mailed Oct. 15, 2013.
(Continued)

*Primary Examiner* — Bot Ledynh
(74) *Attorney, Agent, or Firm* — Koppel, Patrick, Heybl & Philpott

(57) ABSTRACT

A damage detecting device according to one aspect of the present invention comprises a first speed generator, a second speed generator, a first waveform shaping section, a second waveform shaping section, and a determining section. The determining section compares a second rectangular wave shaped by the second waveform shaping section and a first rectangular wave shaped by the first waveform shaping section and, if the first rectangular wave is not output while the second rectangular wave is output, determines that a supporting device for an armature shaft is damaged or worn.

11 Claims, 11 Drawing Sheets

(51) Int. Cl.
  *G01B 7/14*  (2006.01)
  *H02K 7/14*  (2006.01)
  *H02K 11/00* (2016.01)
  *B60L 3/00*  (2006.01)
  *B60W 10/08* (2006.01)
  *H02K 15/16* (2006.01)

(52) U.S. Cl.
  CPC ............... *H02K 11/00* (2013.01); *H02K 11/20* (2016.01); *B60L 2240/421* (2013.01); *B60L 2240/461* (2013.01); *H02K 15/16* (2013.01)

(56) References Cited

U.S. PATENT DOCUMENTS

2007/0222438 A1* 9/2007 Reeves ........................ 324/240
2010/0078527 A1  4/2010 Burkhart et al.
2011/0037461 A1* 2/2011 Braun ........................... 324/240
2013/0006540 A1  1/2013 Sakaguchi et al.

FOREIGN PATENT DOCUMENTS

| JP | 7-43207 A | 2/1995 |
| JP | 2006-189371 A | 7/2006 |
| JP | 2010-527829 A | 8/2010 |
| JP | 2012-58171 A | 3/2012 |
| WO | WO 2011/081085 A1 | 7/2011 |

OTHER PUBLICATIONS

Notification of Transmittal of Translation of the International Preliminary Report on Patentability, from corresponding Application No. PCT/JP2013/071523, dated Feb. 19, 2015.

* cited by examiner

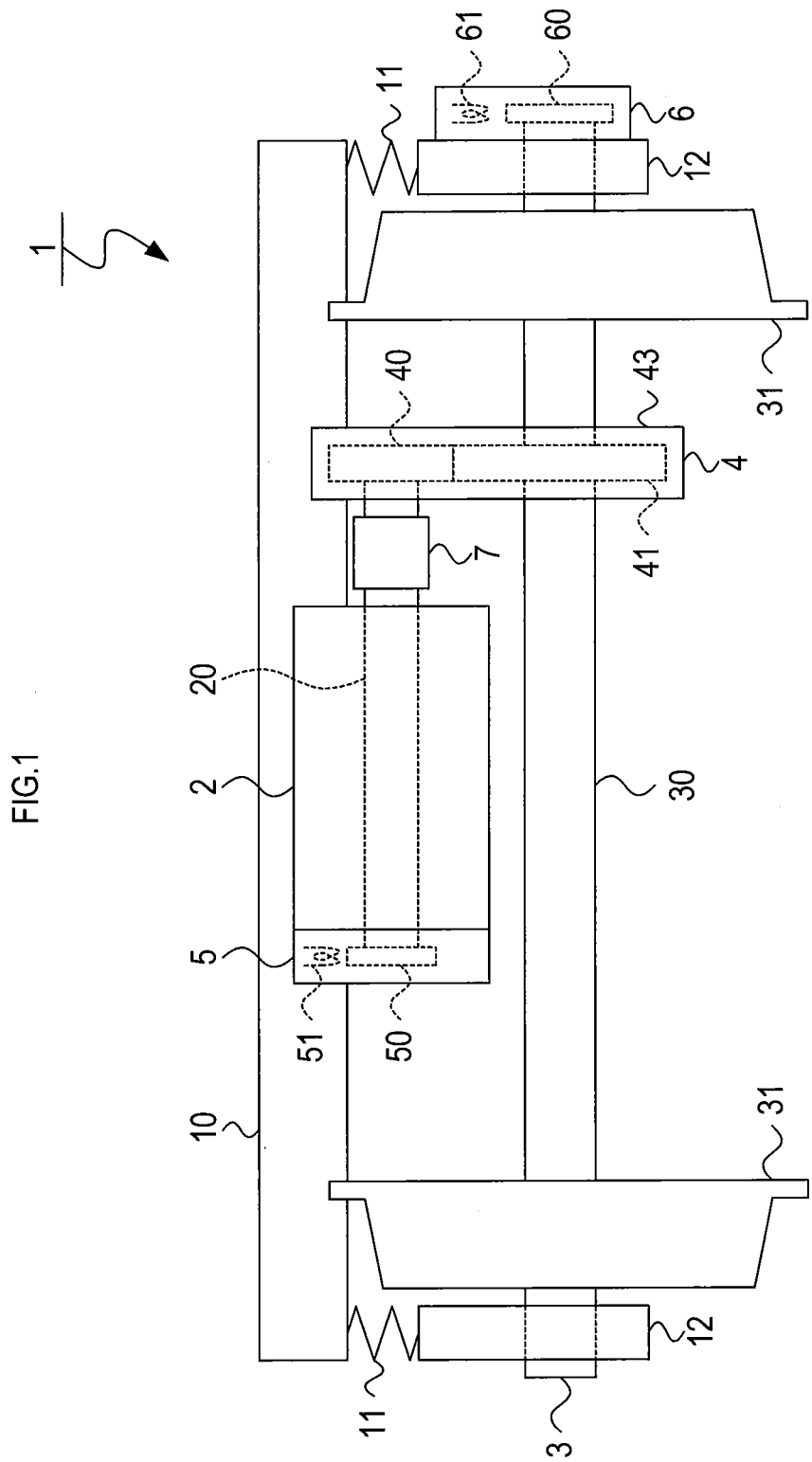

DAMAGE DETECTING DEVICE FOR SUPPORTING STRUCTURE FOR ARMATURE SHAFT

CROSS-REFERENCE TO RELATED APPLICATIONS

This international application claims the benefit of Japanese Patent Application No. 2012-176300 filed Aug. 8, 2012 in the Japan Patent Office, and the entire disclosure of Japanese Patent Application No. 2012-176300 is incorporated herein by reference.

TECHNICAL FIELD

The present invention relates to a damage detecting device for detecting damage to a supporting structure such as a supporting device or the like that rotatably supports an armature shaft.

BACKGROUND ART

Conventionally, in a train, as devices for detecting vehicle speed, speed generators are respectively attached to an armature shaft of an electric motor and an axle of a driving wheel rotated by power received from the electric motor via this armature shaft (Patent Document 1).

This is because not only the train speed is detected, but also whether a power transmission system from the electric motor to the wheel is in an abnormal state or not is detected by a comparison between the output results of these speed generators.

PRIOR ART DOCUMENTS

Patent Documents

Patent Document 1: Japanese Unexamined Patent Application Publication No. 2006-189371

SUMMARY OF THE INVENTION

Problems to be Solved by the Invention

Generally, an electric motor is fixed to a truck frame, and a driving wheel shaft is fixed to the truck frame via a spring or the like. Therefore, the armature shaft and the axle of the driving wheel shaft are connected by a WN joint so that even if the armature shaft is displaced with respect to the axle of the driving wheel shaft, the displacement is absorbed.

Therefore, even if the armature shaft inclines due to wear, damage, or the like of a supporting device such as a roller and the like that rotatably support the armature shaft, power is normally transmitted from the armature shaft to the axle of the driving wheel shaft, and even when results output from the speed generators are compared, no difference arises between them, making it difficult to discover the inclination of the armature shaft.

However, if wear or damage of the supporting device is not discovered while it is minor, the electric motor may be damaged during running of the train.

Accordingly, it is preferable that one aspect of the present invention can provide a damage detecting device that detects, by means of speed generators, damage or wear of a supporting structure, such as a supporting device, which rotatably supports an armature shaft of an electric motor.

Means for Solving the Problems

A damage detecting device according to a first aspect of the present invention is configured to detect damage to a supporting device rotatably supporting an armature shaft of an electric motor, and comprises a first speed generator and a second speed generator.

The first speed generator comprises:

a disk-shaped first inductor attached to the armature shaft, and having recesses and projections formed at equal pitches along a circumference around a same central axis as the armature shaft;

at least one pair of first magnetic pole pieces, one end of each of the first magnetic pole pieces being joined to one of poles of a first permanent magnet, and the other end of each of the first magnetic pole pieces being disposed opposite the recesses and projections of the first inductor; and a first coil that detects a change in a magnetic flux passing through the first magnetic pole pieces and generates an output voltage of a waveform corresponding to this detection.

The second speed generator comprises:

a disk-shaped second inductor attached to an axle of a driving wheel shaft to which power from the electric motor is transmitted via the armature shaft, and having recesses and projections formed at equal pitches along a circumference around a same central axis as the axle;

at least one pair of second magnetic pole pieces, one end of each of the second magnetic pole pieces being joined to one of poles of a second permanent magnet, and the other end of each of the second magnetic pole pieces being disposed opposite the recesses and projections of the second inductor; and a second coil that detects a change in a magnetic flux passing through the second magnetic pole pieces and generates an output voltage of a waveform corresponding to this detection.

The device further comprises:

a first waveform shaping section that converts the output voltage, generated in the first coil, into a first rectangular wave based on a preset first threshold value;

a second waveform shaping section that shapes the output voltage, generated in the second coil, into a second rectangular wave based on a preset second threshold value; and a determining section that compares the second rectangular wave and the first rectangular wave and, if the first rectangular wave is not output while the second rectangular wave is output, determines that the supporting device is damaged or worn.

When the inclination of the armature shaft increases due to damage to or wear of the supporting device supporting the armature shaft, the distance between a projecting part of the first inductor and the first magnetic piece included in the first speed generator increases, resulting in a decrease in voltage output from the first coil.

On the other hand, if the power transmission system is not in an abnormal state even when the armature shaft inclines, there is no change in the magnitude of voltage output from the second coil included in the second speed generator.

Therefore, a comparison between the first rectangular wave and the second rectangular wave, both of which correspond to these output voltages, may indicate a case where, when the armature shaft inclines due to damage to or wear of the supporting device, the first rectangular wave is not output while the second rectangular wave is output.

That is, through the determination whether there is a case where the first rectangular wave is not output while the second rectangular wave is output, the damage detecting device according to the present invention determines whether the supporting device rotatably supporting the armature shaft is damaged or worn.

Accordingly, the damage detecting device according to the present embodiment makes it possible to securely detect, by use of the first speed generator on the armature shaft and the second speed generator on the axle of the driving wheel shaft, damage to or wear of the supporting structure, such as the supporting device rotatably supporting the armature shaft of the electric motor.

The power transmission system may comprise a displacement absorption type transmission section, such as a WN joint, which transmits power while absorbing displacement between the armature shaft and the rotation axis of the driving wheel shaft, or a gear type transmission section, such as a decelerator, which has a plurality of gears.

The first inductor may be attached to one end of the both ends of the armature shaft in the axial direction thereof. The one end is opposite the other end located on the side where power is transmitted to the axle of the driving wheel shaft.

The second inductor may be attached to one end of the axle of the driving wheel shaft.

The recesses and projections of each of the first and second inductors may be formed around the entire edge of the corresponding disk.

The first and second threshold values may be equal or unequal. However, the first threshold value may have the magnitude verified by an experiment or the like on the assumption that this threshold value arises when the distance between a projecting part of the first inductor and the first magnetic pole piece changes due to damage to or wear of the supporting device.

A damage detecting device according to a second aspect of the present invention is configured to detect damage to a supporting device rotatably supporting an armature shaft of an electric motor, and comprises a speed generator.

The speed generator comprises:

a disk-shaped inductor attached to the armature shaft, and having recesses and projections formed at equal pitches along a circumference around a same central axis as the armature shaft;

at least one pair of first magnetic pole pieces, one end of each of the first magnetic pole pieces being joined to one of poles of a first permanent magnet, and the other end of each of the first magnetic pole pieces being disposed opposite the recesses and projections of the inductor;

a first coil that detects a change in a magnetic flux passing through the first magnetic pole pieces and generates an output voltage of a waveform corresponding to this detection;

at least one pair of second magnetic pole pieces, one end of each of the second magnetic pole pieces being joined to one of poles of a second permanent magnet, and the other end of each of the second magnetic pole pieces being disposed opposite the recesses and projections of the inductor; and a second coil that detects a change in a magnetic flux passing through the corresponding second magnetic pole pieces and generates an output voltage of a waveform corresponding to this detection.

The device further comprises:

a first waveform shaping section that converts the output voltage, generated in the first coil, into a first rectangular wave based on a preset first threshold value;

a second waveform shaping section that shapes the output voltage, generated in the second coil, into a second rectangular wave based on a preset second threshold value; and a determining section that compares the second rectangular wave and the first rectangular wave and determines, if the first rectangular wave is not output while the second rectangular wave is output, that the supporting device is damaged or worn.

Providing the speed generator corresponding to the first speed generator in the first aspect of the present invention with the second magnetic pole pieces and the second coil, as in the present invention, also makes it possible to detect damage to or wear of a supporting structure, such as the supporting device rotatably supporting the armature shaft of the electric motor. For example, if the armature shaft inclines in a vertical direction in a case where the first magnetic pole pieces and the first coil are arranged above the inductor and the second magnetic pole pieces and the second coil are arranged to the right of the inductor, the distance of the first magnetic piece from the inductor increases. However, the possibility that the distance of the second magnetic piece from the inductor increases as much as the distance of this first magnetic piece is small. As a result, voltage output from the first coil decreases, but there is almost no change in voltage output from the second coil. Therefore, according to the present invention, as with the damage detecting device in the first aspect of the present invention, damage to or wear of the supporting structure, such as the supporting device rotatably supporting the armature shaft of the electric motor, can securely be detected.

In a third aspect of the present invention, the determining section compares the second rectangular wave and the first rectangular wave and, if a duration for which the first rectangular wave is not output while the second rectangular wave is output continues for a predetermined duration, determines that the supporting device is damaged or worn. The armature shaft may be inclined by vibration. Such a configuration makes it possible to distinguish inclination caused by vibration from inclination not caused by vibration.

As in a fourth aspect of the present invention, the determining section may compare a speed calculated from the first rectangular wave and a speed calculated from the second rectangular wave and, may determine, if the speed difference is equal to or larger than a predetermined speed difference, that the supporting device is damaged or worn.

As in a fifth aspect of the present invention, the first threshold value may be higher than the second threshold value. Thus, if the supporting structure such as the supporting device is damaged or worn, output of a rectangular wave from the first waveform shaping section is immediately stopped by virtue of the high first threshold value, thus enabling the determining section to make a prompt determination.

A damage detecting device according to a sixth aspect of the present invention is configured to detect damage to a supporting device rotatably supporting an armature shaft of an electric motor, and comprises a speed generator.

The speed generator comprises:

a disk-shaped inductor attached to the armature shaft of the electric motor, and having recesses and projections formed at equal pitches along a circumference around a same central axis as the armature shaft;

at least one pair of magnetic pole pieces, one end of each of the magnetic pole pieces being joined to one of poles of a permanent magnet, and the other end of each of the magnetic pole pieces being disposed opposite the recesses and projections of the inductor; and a coil that detects a change in a magnetic flux passing through the magnetic pole pieces and generates an output voltage of a waveform corresponding to this detection.

This damage detecting device further comprises:

a recording section that records, in a time series, the output voltage of the coil; and a determining section that determines that, if the output voltage recorded by the recording section is equal to or smaller than a predetermined threshold value, the supporting device is damaged or worn.

Thus, checking the output voltage from the first coil, recorded in a time series, makes it possible to check the process of damage to or wear of the supporting device. Additionally, checking whether the output voltage is equal to or smaller than the first threshold value or not makes it possible to immediately check whether the supporting device is damaged.

As in a seventh aspect of the present invention, the damage detecting device in the sixth aspect of the present invention may comprise a speed detecting section that detects speed of a train running by receiving power from the electric motor. The recording section may record the output voltage when the speed detected by the speed detecting section is equal to or higher than a certain speed.

Additionally, as in an eighth aspect of the present invention, the damage detecting device of the seventh aspect of the present invention may record the speed detected by the speed detecting section, together with the output voltage.

BRIEF DESCRIPTION OF THE DRAWINGS

FIG. 1 is a schematic view of a truck according to a first embodiment.

EXPLANATION OF REFERENCE NUMERALS

Figure 2A:
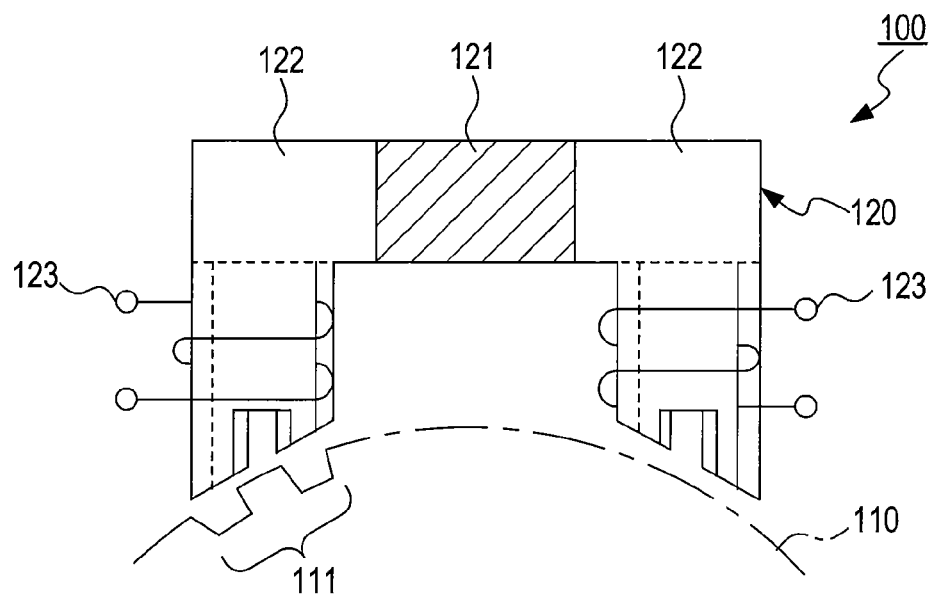
FIGS. 2A-2B are schematic views illustrating a basic structure of a speed generator.

1 . . . truck, 2 . . . electric motor, 3 . . . driving wheel shaft, 4 . . . decelerator, 5 . . . first speed generator, 6 . . . second speed generator, 7 . . . WN joint, 9 . . . BPG, 10 . . . truck frame, 11 . . . spring, 12 . . . axle box, 20 . . . armature shaft, 21 . . . coil, 22 . . . ball bearing, 23 . . . roller bearing, 30 . . . axle, 31 . . . wheel, 40 . . . small gear, 41 . . . large gear, 50 . . . inductor, 51 . . . coil, 52 . . . iron core, 60 . . . inductor, 61 . . . coil, 90 . . . first filtering section, 91 . . . first waveform shaping section, 92 . . . first speed calculating section, 93 . . . second filtering section, 94 . . . second waveform shaping section, 95 . . . second speed calculating section 96 . . . speed comparing section, 97 . . . monitor output section, 100 . . . speed generator, 110 . . . inductor 111 . . . recesses and projections, 120 . . . generator part, 121 . . . permanent magnet, 122 . . . iron core, 123 . . . coil

MODE FOR CARRYING OUT THE INVENTION

Hereinafter, embodiments according to the present invention will be described with reference to the drawings.

First Embodiment

Truck

A truck 1 according to the embodiment is a truck for driving wheels of Shinkansen trains or other trains.

This truck 1 comprises an electric motor 2, a driving wheel shaft 3, a decelerator 4, a first speed generator 5, a second speed generator 6, and a WN joint 7.

The electric motor 2 is fixed to a truck frame 10 of the truck 1, and axially rotates an armature shaft 20, thereby outputting generated power.

The driving wheel shaft 3 comprises an axle 30 and a pair of wheels 31 attached to near both ends of the axle 30. Axle boxes 12 are fixed to the truck frame 10 via springs 11. The axle 30 is rotatably supported by the axle boxes 12, thereby the driving wheel shaft 3 is fixed to the truck frame 10 so as to be displaceable. Accordingly, when a train is subjected to vibration or a train body inclines on a curve, the armature shaft 20 is displaced with respect to the axle 30 of the driving wheel shaft 3. Therefore, the armature shaft 20 is connected to this axle 30 via the WN joint 7.

The decelerator 4 comprises a small gear 40 and a large gear 41. The gears 40, 41 are accommodated in a case 43 so as to engage with each other and be axially rotatable. Of these, the large gear 41 is fixed on the axle 30 so as to rotate around the same axis as the axle 30, and the small gear 40 is connected to the armature shaft 20 of the electric motor 2 via the WN joint 7 so as to rotate around the same axis as the armature shaft 20.

The first speed generator 5 is fixed to the electric motor 2, and comprises a disk-shaped inductor 50 and coil 51, which generates induced electromotive force by the rotation of this inductor 50.

Of these, the inductor 50 is fixed to one of the both ends of the armature shaft 20 in the axial direction thereof, the one end being located on the side where the WN joint is not connected. This inductor 50 rotates together with the armature shaft 20 around the same axis as the armature shaft 20.

The second speed generator 6 is fixed to the axle box 12, and comprises a disk-shaped inductor 60 and coil 61, which generates induced electromotive force by the rotation of this inductor 60.

Of these, the inductor 60 is fixed to one of the both ends of the axle 30 of the driving wheel shaft 3 in the axial direction thereof, and rotates together with the axle 30 around the same axis as the axle 30.

[Speed Generator]

Figure 2B:
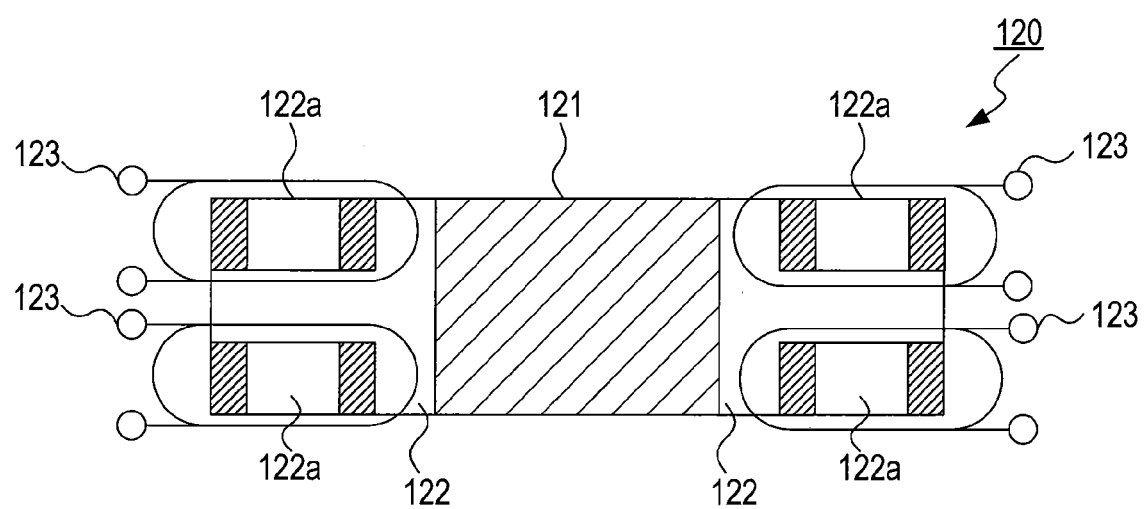

Referring to FIGS. 2A, 2B, next will be described the respective basic configurations and operations of the speed generators used as the first speed generator 5 and second speed generator 6 described above.

As shown in FIG. 2A, a speed generator 100 comprises an inductor 110 and a generator part 120.

The inductor 110 is disk-shaped and the entire edge of the disk has recesses and projections 111 at equal pitches (FIG. 2A shows only a portion facing to a generator part 120, and also shows only part of the recesses and projections 111).

The generator part 120 comprises a permanent magnet 121, a pair of iron cores 122, and a pair of coils 123.

Each iron core 122 extends in an L shape from the corresponding pole of the permanent magnet 121 towards the disk edge part of the inductor 110, and each coil 123 is wound around the corresponding iron core 122.

The speed generator 100 with the foregoing configuration forms a magnetic circuit from one pole of the permanent magnet 121, via the one iron core 122 connected to this pole side and also via the inductor 110, to the other iron core 122 and then to the other pole of the permanent magnet 121.

Additionally, in the speed generator 100, when the inductor 110 rotates, the distance between the end part of each iron core 122 facing to the inductor 110, and the edge part of the inductor 110 is changed by the recesses and projections 111 of the edge part of the inductor 110.

Accordingly, when the inductor 110 rotates, a magnetic flux crossing each iron core 122 changes, and induced electromotive force is generated at both ends of each coil 123 by this magnetic flux change. Detecting the induced electromotive forces enables the detection of the speed of a rotor that has the inductor 110 attached thereto.

In the present embodiment, the inductor 50 of the first speed generator 5 and the inductor 60 of the second speed generator 6 each correspond to the inductor 110 of the speed generator 100 described above, and the coil 51 of the first speed generator 5 and the coil 61 of the second speed generator 6 each correspond to the coils 123 of the speed generator 100.

While not shown in FIG. 1, as the foregoing description of the speed generator 100, each of the first and second speed generators 5 and 6 has a configuration corresponding to the permanent magnet 121 and iron cores 122.

At least one pair of iron cores 122 may be provided. Additionally, as with the iron cores 122 shown in FIG. 2B, iron cores to be used may have bifureated portions opposite to the inductor 110. Furthermore, another iron core may be provided outside each iron core 122.

As shown in FIG. 2B, a coil 123 may be provided on each of the two branches 122a of each iron core or may be wound around the entirety of iron cores 122 even in the case of the bifurcated iron core 122.

In a case where one pair or more of iron cores 122 are provided, a coil 51 may be provided on each iron core 122.

Figure 3:
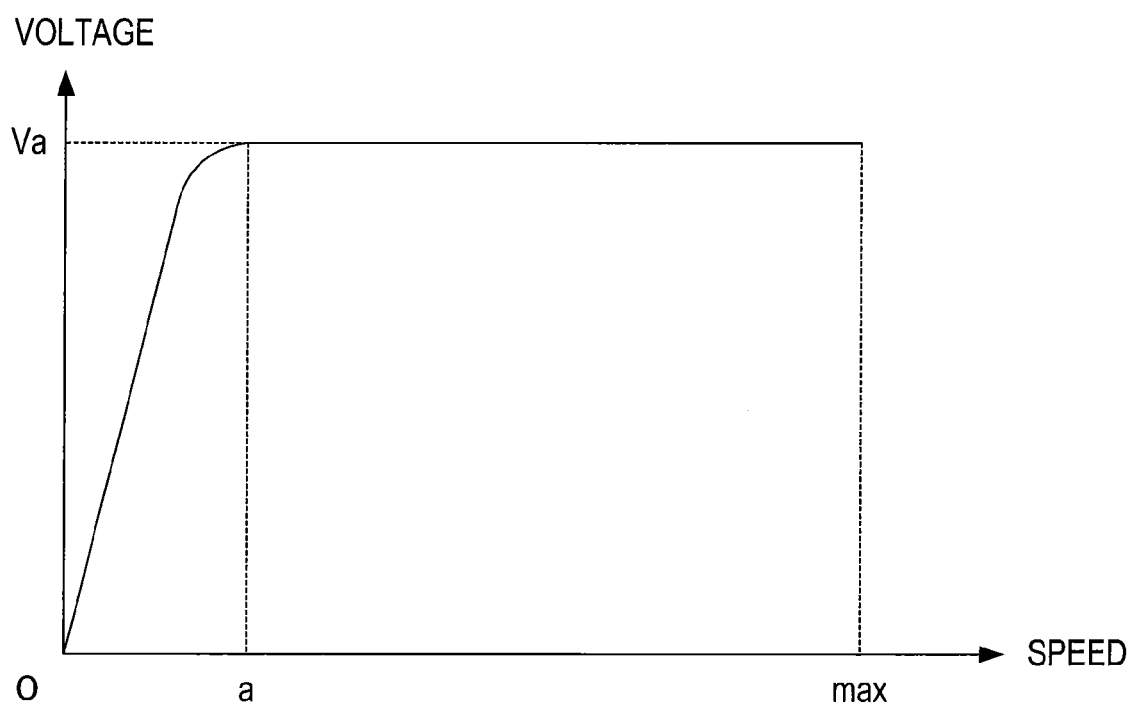
FIG. 3 is a graph showing a relationship between voltage output from the speed generator and speed of a train car.

In the speed generator 100 according to the present embodiment, as shown in FIG. 3, if there is no change in the corresponding distances between the iron core 122 and inductor 110, the magnetic flux saturates when the truck runs at a speed value "a" or higher. Consequently, voltage output from the coil 123 is substantially constant.

The damage to or wear of ball bearing or roller bearing, described below, is detected when the voltage output from the coils 123 have become approximately constant.

Each of first and second threshold values, described below, is set based on a voltage value when the distance between the iron core 122 and the inductor 110 is equal to a distance in initial setting, and voltage output from the coil 123 has become approximately constant.

[Supporting Structure for Armature Shaft]

Next, a supporting structure for the armature shaft of the electric motor 2 will be described with reference to FIGS. 4A, 4B.

Figure 4A:
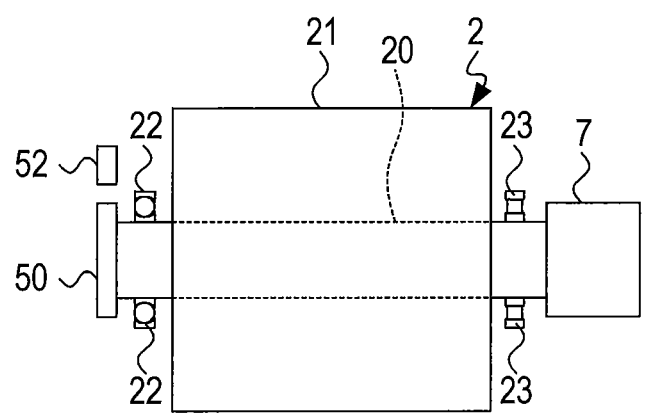
FIGS. 4A-4B are schematic views of a supporting structure for an armature shaft.

As shown in FIG. 4A, the electric motor 2 according to the present embodiment comprises the armature shaft 20, and a cylindrical coil 21 disposed on the same axis as the armature shaft 20.

Additionally, this electric motor 2 has a not shown housing that accommodates the whole coil 21 and is fixed to the truck frame 10. The housing comprises a plurality of ball bearings 22 and a plurality of roller bearings 23, both of which are arranged at equal intervals around the armature shaft 20 and rotatably support the armature shaft 20.

Of these, the ball bearing 22 is arranged between the coil 21 and the inductor 50 of the first speed generator 5, thereby supporting the armature shaft 20. The roller bearing 23 is arranged between the coil 21 and the WN joint 7, thereby supporting the armature shaft 20.

Figure 4B:
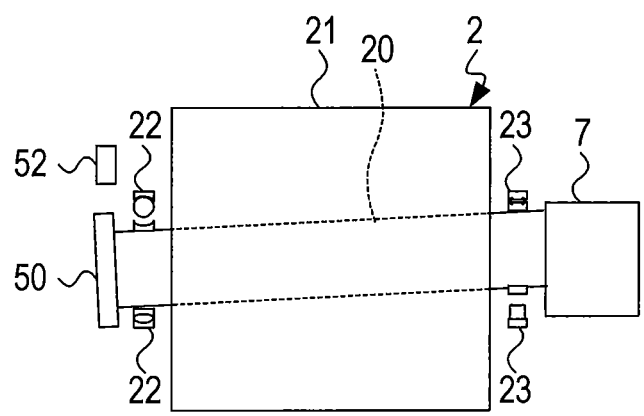

In FIGS. 4A, 4B, as a configuration corresponding to the iron core 122 of the speed generator 100 described above, an iron core 52 of the first speed generator 5 is shown.

[BGP]

Next, referring to the block diagram in FIG. 5, a description will be given of a mechanism for speed detection by a BPG (Brake Pattern Generator) installed in a train that comprises the foregoing truck 1.

This BPG 9 corresponds to an example of the damage detecting device according to the present invention.

Figure 5:
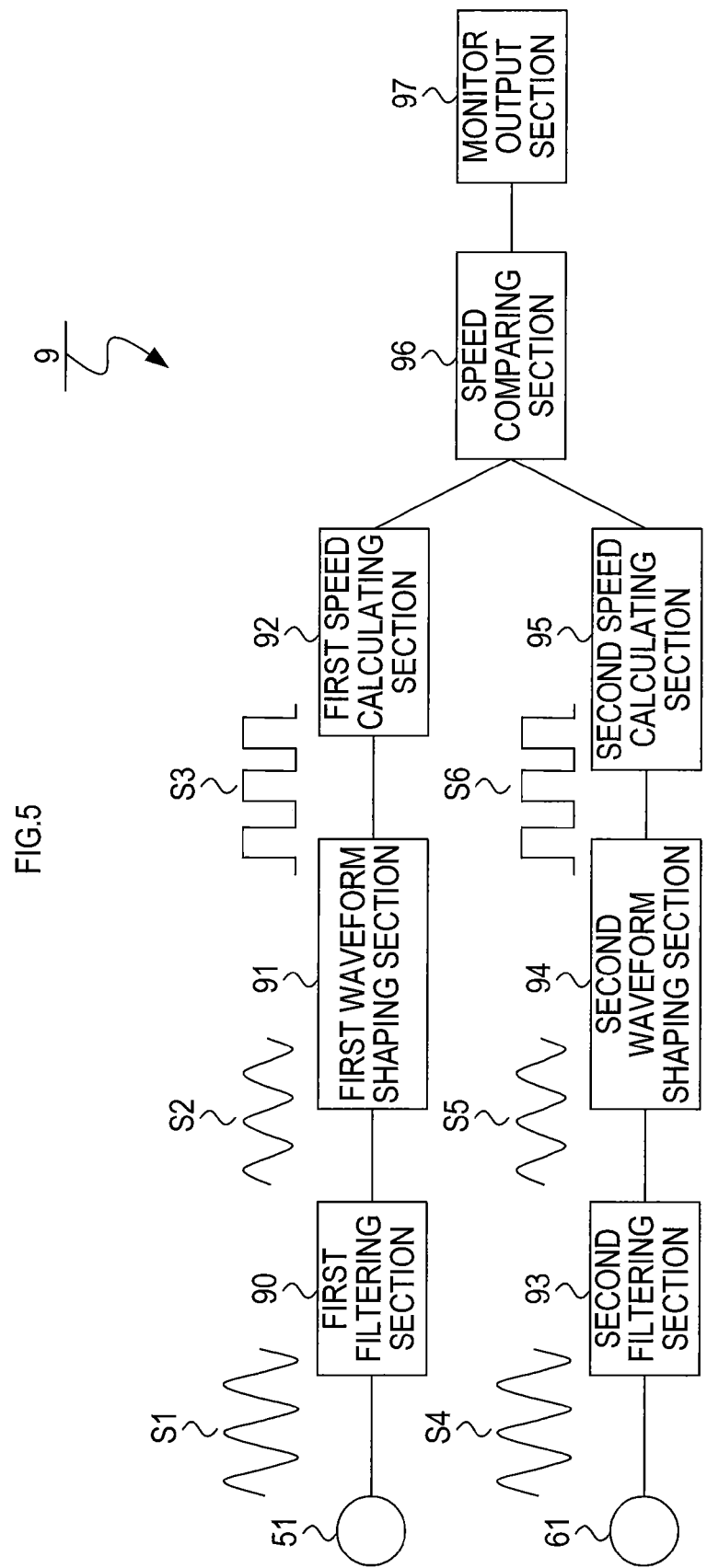
FIG. 5 is a block diagram of a BPG according to the first embodiment (Normal state).

FIG. 5 schematically shows signals (S1 to S6), each of which is output from one of the coil 51, a later-described first filtering section 90, a first waveform shaping section 91, the coil 61, a later-described second filtering section 93, or a second waveform shaping section 94.

The BPG 9 according to the present embodiment comprises the first filtering section 90, the first waveform shaping section 91, a first speed calculating section 92, the second filtering section 93, the second waveform shaping section 94, a second speed calculating section 95, a speed comparing section 96, and a monitor output section 97.

The first filtering section 90 is a filter that removes noise superposed on a voltage signal (S1) resulting from induced electromotive force generated by the coil 51 of the first speed generator 5.

The first waveform shaping section 91 performs the process of shaping a voltage signal (S2) from which noise is removed by the first filtering section 90 into a rectangular wave (S3) by dividing the voltage signal (S2) into a component that has a voltage equal to or higher than a predetermined first threshold value and a component that has a voltage equal to or lower than the first threshold value.

This first threshold value is set in advance, by experiment or the like, to a value corresponding to an estimated voltage value of induced electromotive force to be generated in the coil 21 when the armature shaft 20 inclines due to damage to or wear of the ball bearing 22 or the roller bearing 23 with the result that the iron core 52 separates from a projecting part of the recesses and projections (corresponding to the recesses and projections 111) of the circumference of the inductor 50 by a predetermined distance or greater, which is a determinable distance.

The first speed calculating section 92 performs the process of counting rectangular waves per unit time output from the first waveform shaping section 91 and calculating the speed of the train from the operating state of the electric motor 2.

The second filtering section 93 is a filter that removes noise superposed on a voltage signal (S4) resulting from induced electromotive force generated in the coil 61 of the second speed generator 61.

The second waveform shaping section 94 performs the process of shaping a voltage signal (S5) from which noise is removed by the second filtering section 93 into a rectangular wave (S6) by dividing the voltage signal (S5) into a component that has a voltage equal to or higher than a predetermined second threshold value and a component that has a voltage equal to or lower than the second threshold value.

The second speed calculating section 95 performs the process of counting rectangular waves per unit time output from the second waveform shaping section 94 and calculating the speed of the train from the rotating state of the driving wheel shaft 3.

The speed comparing section 96 compares the train speeds calculated by the first speed calculating section 92 and second speed calculating section 95, and determines the train speed.

The monitor output section 97 performs the process of outputting the result of the comparison by the speed comparing section 96 to a not shown monitor that is provided in the driver's cab of the train or elsewhere.

The first threshold value is set higher than the second threshold value.

(Detection of Damage to or Wear of Ball Bearing or Roller Bearing)

Next will be described a detection method for damage to or wear of the ball bearing 22 or the roller bearing 23 by use of the first speed generator 5, second speed generator 6, and BPG 9 described above.

If the ball bearing 22 or the roll bearing 23 is damaged or worn, the armature shaft 20 of the electric motor 2 inclines, as shown in FIG. 4B, and consequently the inductor 50 attached to one end of the armature shaft 20 moves away from the generator part that comprises the coil 51, etc.

Figure 6:
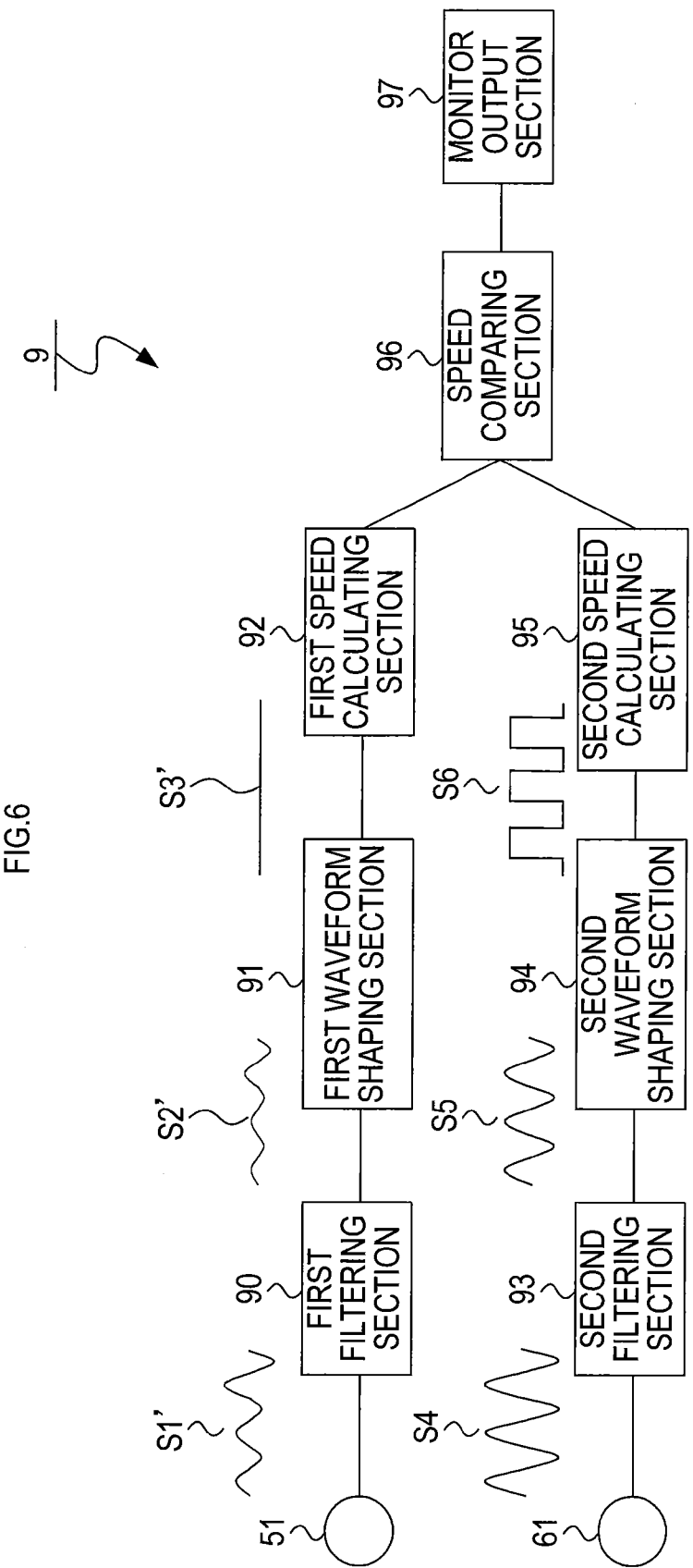
FIG. 6 is a block diagram of the BPG according to the first embodiment (Damaged state).

When the inductor 50 moves away from the generator part in such a manner, the induced electromotive force generated in the coil 51 of the first speed generator 5 become smaller (S1') than those generated before the inclination of the armature shaft 20, as shown in FIG. 6. As a result, a rectangular wave (S2') is not output from the first waveform shaping section 91.

Consequently, a difference arises between the speeds calculated by the first speed calculating section 92 and the second speed calculating section 95. Accordingly, from this speed difference, the speed comparing section 96 detects the inclination of the armature shaft 20.

In the present embodiment, when, for example, a speed difference of 3 km/h or higher continues for five minutes or longer in this speed comparing section 96, a determination is made that the ball bearing 22 or the roller bearing 23 is worn or damaged and hence the armature shaft 20 is inclined. The determination result is output in the form of a warning to the monitor in the driver's cab or elsewhere, via the monitor output section 97.

(Operation and Effects of the Present Embodiment)

Each configuration of the foregoing embodiment exhibits operation and effects, as described below.

When the inclination of the armature shaft 20 increases due to damage to or wear of the ball bearing 22 or the roller bearing 23 supporting the armature shaft 20, the distance between the projecting part of the inductor 50 included in the first speed generator 5 and the iron core included in the first speed generator 5 increases, resulting in low voltage output from the coil 51.

On the other hand, if the power transmission system is not in an abnormal state even when the armature shaft 20 inclines, there is no change in the magnitude of the voltage output from the coil 61 included in the second speed generator 6.

Therefore, a comparison between a first rectangular wave (output from the first waveform shaping section 91) and a second rectangular wave (output from the second waveform shaping section 94), both of which correspond to the output voltages, may indicate the case where, when the armature shaft 20 inclines due to damage to or wear of the ball bearing 22 or the roller bearing 23, the first rectangular wave is not output while the second rectangular wave is output.

That is, through the determination made by the speed comparing section 96 whether there is a case where the first rectangular wave is not output while the second rectangular wave is output, the BPG 9 according to the present embodiment determines whether the ball bearing 22 or the roller bearing 23 is damaged or worn.

Accordingly, the BPG 9 according to the present embodiment makes it possible to securely detect damage to or wear of the ball bearing 22 or the roller bearing 23 by use of the first speed generator 5 on the armature shaft 20 and the second speed generator 6 on the axle of the driving wheel shaft 3.

In the present embodiment, if a constant speed difference continues for five seconds or longer, a determination is made that the ball bearing 22 or the roller bearing 23 is damaged or worn. This is because since the armature shaft 20 may incline due to vibration, a determination is made whether this inclination has resulted from vibration or not. This duration is not limited to five seconds.

The threshold values used in the first waveform shaping section 91 and the second waveform shaping section 94 may be equal. However, for higher detection accuracy, the threshold value used in the first waveform shaping section 91 may be higher than that used in the second waveform shaping section 94. Thus, if the ball bearing 22 or the roller bearing 23 is damaged or worn, output of a rectangular wave from the first waveform shaping section 91 is immediately stopped by virtue of the high threshold value, thus enabling the speed comparing section 96 to make a prompt determination.

In the foregoing embodiment, a speed difference is detected. However, if a rectangular wave is not output from the second waveform shaping section 94 continuously for a fixed time period while a rectangular wave is output from the second speed calculating section 95, as a result of the direct comparison between the results of the outputs from the first and second speed calculating sections 92 and 95, a determination may be made that the ball bearing 22 or the roller bearing 23 is damaged or worn.

(Corresponding Relation between Configuration of the Present Invention and Configuration of the Present Embodiment)

The inductor 50 corresponds to one example of a first inductor according to the present invention, the iron core 52 corresponds to one example of a first magnetic pole piece according to the present invention, and the coil 51 corresponds to one example of a first coil according to the present invention.

The inductor 60 corresponds to one example of a second inductor according to the present invention, the iron core included in the generator part of the second speed generator 6 corresponding to the iron core 122 corresponds to one example of a second magnetic pole piece according to the present invention, and the coil 61 corresponds to one example of a first coil according to the present invention.

Second Embodiment

Next, a second embodiment according to the present invention will be described.

In the description below, only respects different from the first embodiment will be described.

The present embodiment differs from the first embodiment in respect that the truck 1 does not comprise a configuration corresponding to the second speed generator 6 according to the first embodiment.

Figure 7:
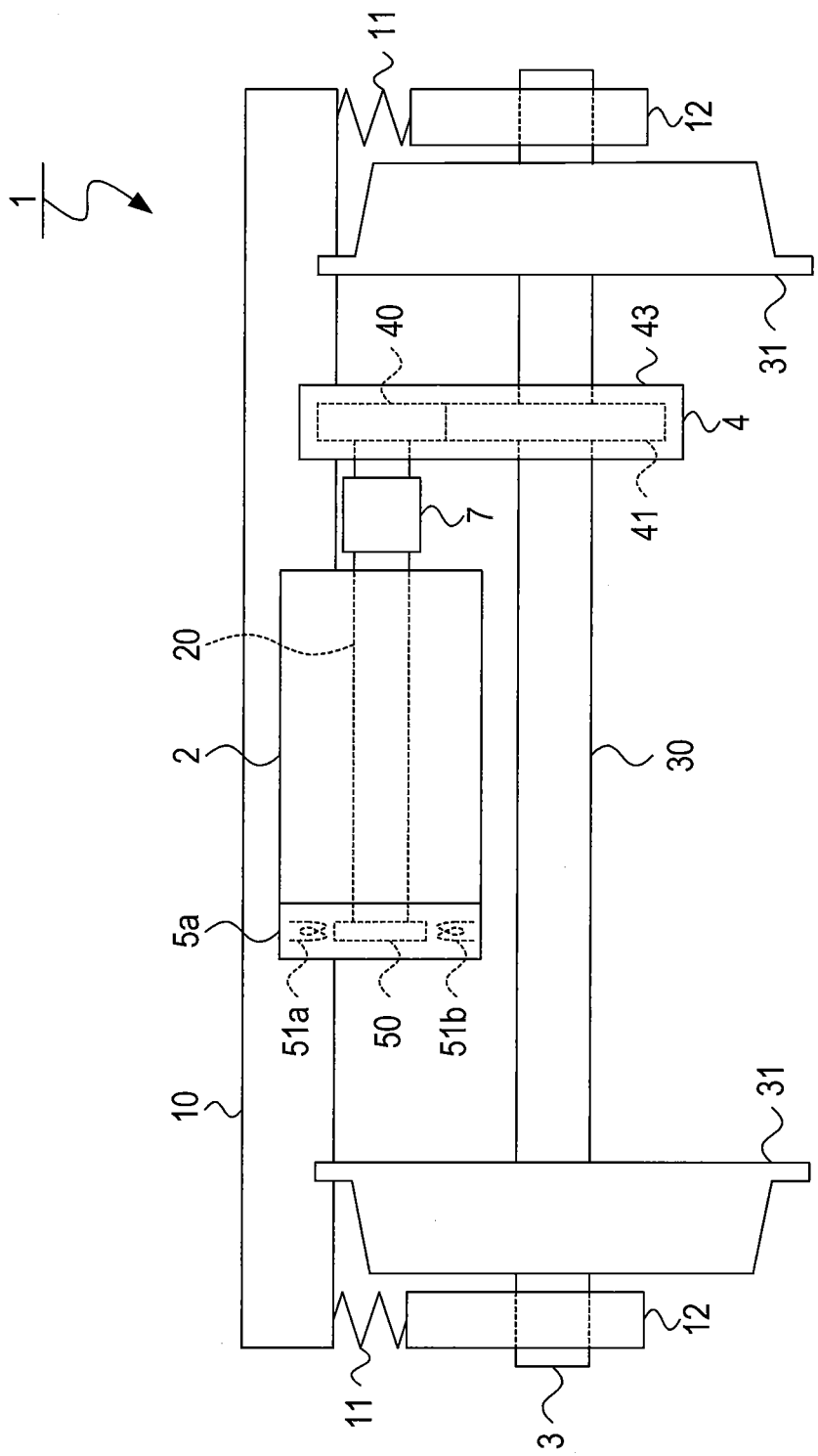
FIG. 7 is a schematic view of a truck according to a second embodiment.

Additionally, the present embodiment, as shown in FIG. 7, differs from the first embodiment in respect that a speed generator 5a corresponding to the first speed generator 5 according to the first embodiment comprises a first generator part having the aforementioned coil 51a, and a second generator part having a coil 51b.

Figure 8:
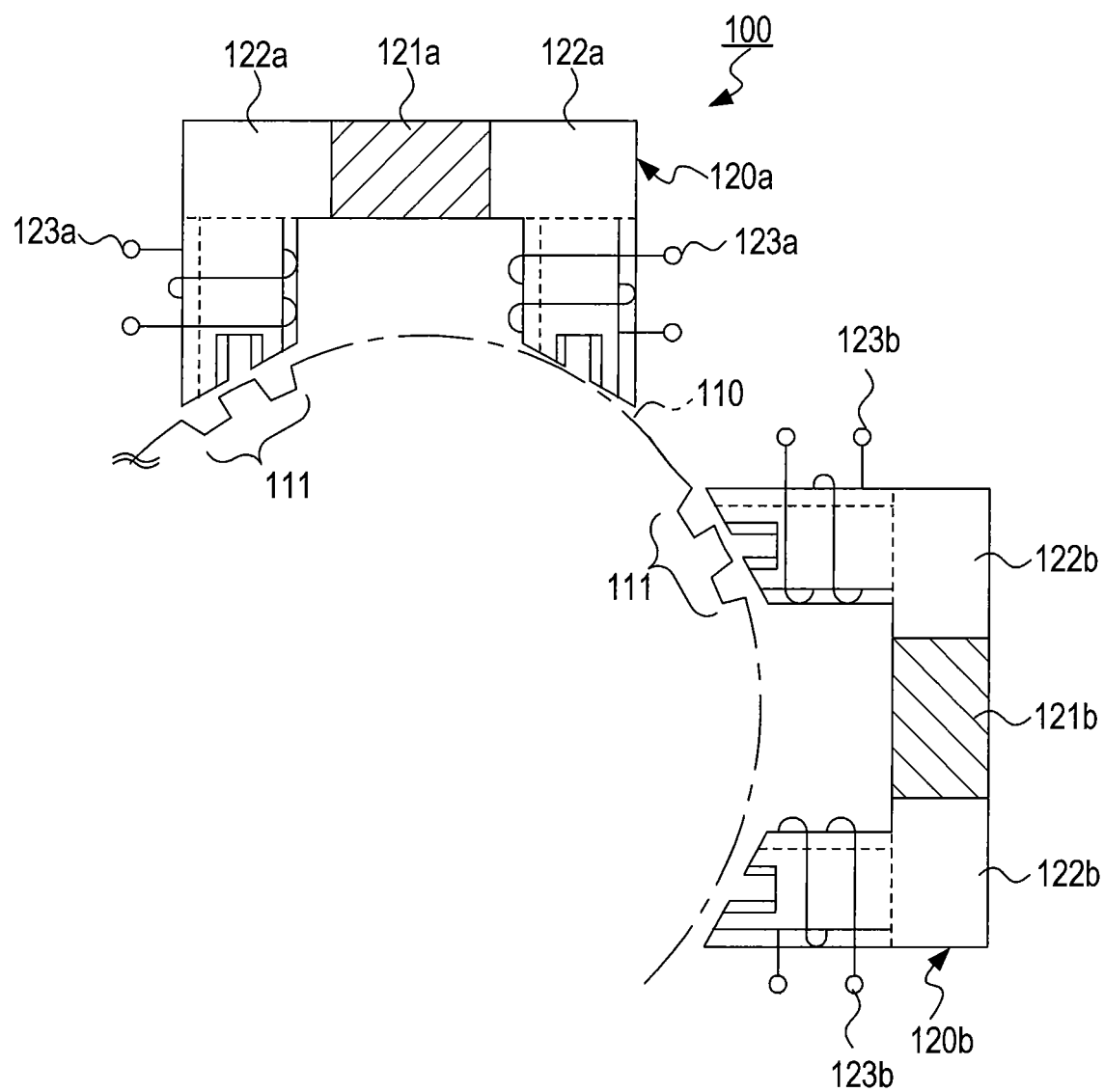
FIG. 8 is a schematic view illustrating a basic structure of a speed generator.

In the present embodiment, the coil 51b is disposed on the right side (on the left side also suffices) as shown in FIG. 8. However, it is shown in a lower position in FIG. 7 for convenience. The coil 51b may be provided in a lower position in FIG. 8.

A basic structure for the speed generator 5a will now be described. As shown in FIG. 8, the basic structure comprises: one inductor 110 as a configuration corresponding to the speed generator 100 described in the first embodiment; and two generator parts 120a, 120b. FIG. 8 shows an example where the two generator parts 120a, 120b are provided above and to the left of respectively, the inductor 110. The structure of each of the two generator parts 120a, 120b is identical to that of the generator part 120 shown in the first embodiment. Therefore, in FIG. 8, structures corresponding to those in FIG. 2 are indicated by adding signs "a", "b" to the signs with which the corresponding structures are labelled.

The coils 51a, 51b correspond to the respective coils 123a, 123b of the generator parts 120a, 120b respectively.

Additionally, the BPG 9 in the first embodiment compares induced electromotive force generated in the coil 51 of the first speed generator 5 and induced electromotive force generated in the coil 61 of the second speed generator 6 (see FIGS. 5, 6). However, as shown in FIGS. 9, 10, the BPG 9 in the present embodiment differs from that in the first embodiment in respect that BPG 9 detects damage to or wear of the ball bearing 22 or the roller bearing 23 by comparing the induced electromotive force generated in the coil 51a and the induced electromotive force generated in the coil 51b of the speed generator 5a.

Figure 9:
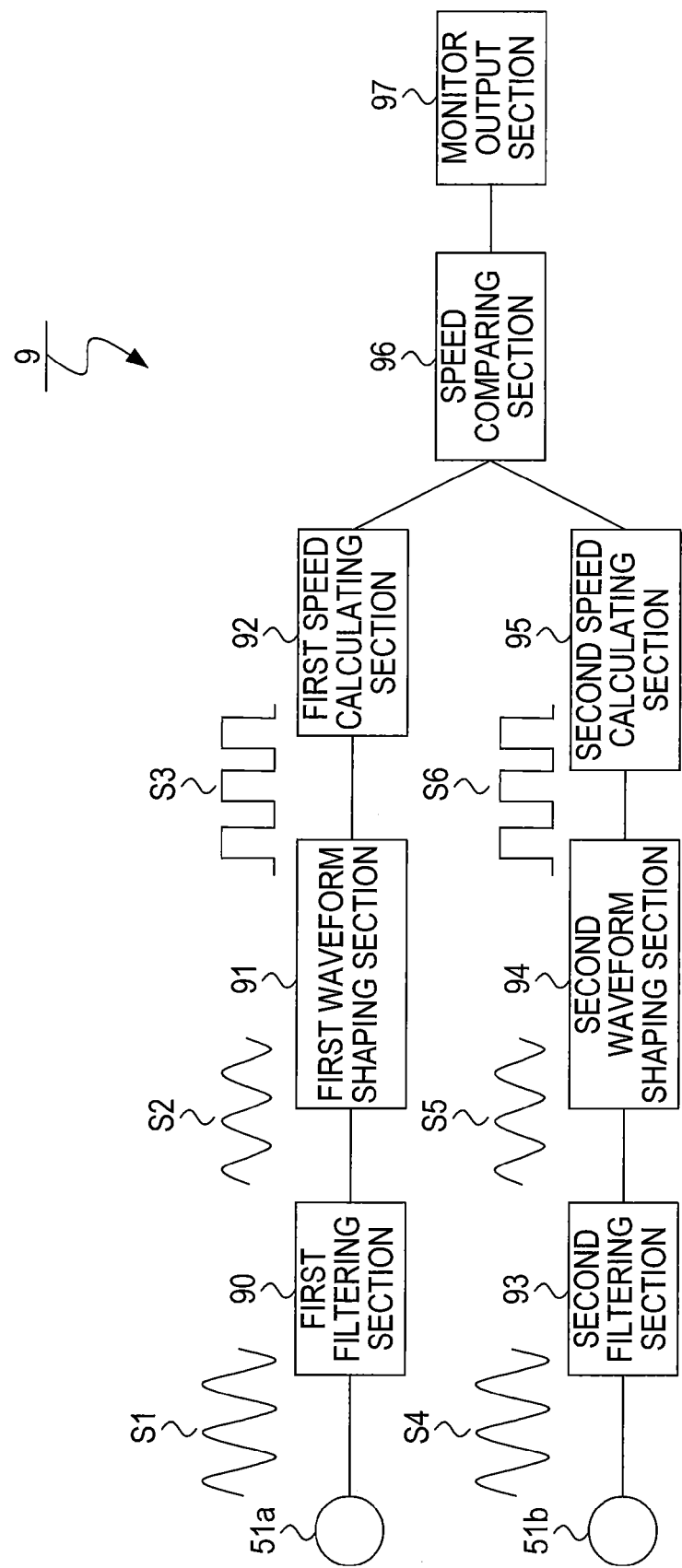
FIG. 9 is a block diagram of a BPG according to the second embodiment (Normal state).

According to the embodiment, as shown in FIG. 9, if there is no damage to or wear of the ball bearing 22 or the roller bearing 23, the output results are the same regardless of the magnitudes of the threshold values.

Figure 10:
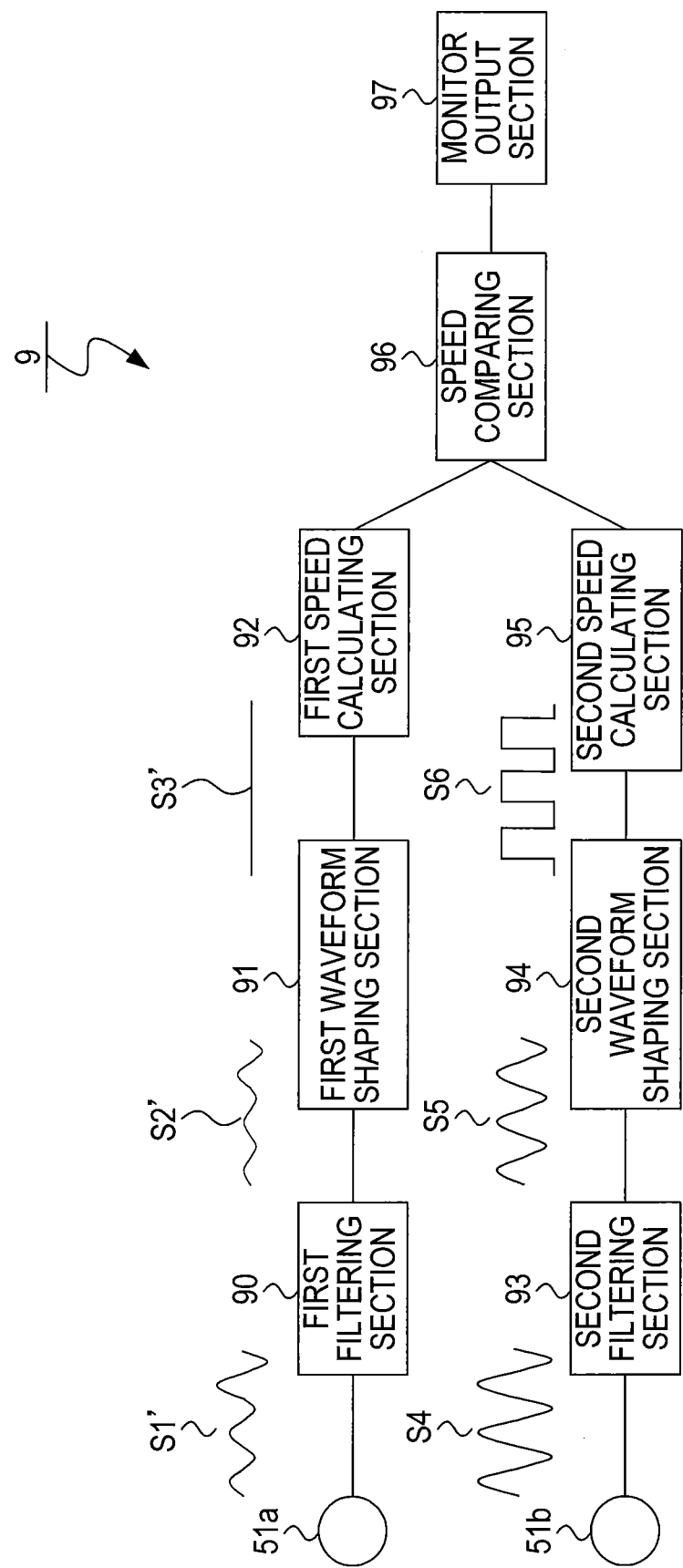
FIG. 10 is a block diagram of the BPG according to the second embodiment (Damaged state).

However, if these bearings are damaged or worn, and the damage or wear is detected in the ball bearing 22 and the roller bearing 23 in either generator part, a rectangular wave is not output from the one generator part, as shown in FIG. 10. Specifically, for example, when the armature shaft 20 inclines downward, the distance between the inductor 110 and the iron core around which upper coil 51a wound increases, but there is no change in the distance between the inductor 110 and the iron core around which the left coil 51b is wound. In such a case, a phenomenon as shown in FIG. 10 arises. Accordingly, as with the first embodiment, the configuration in the present embodiment makes it possible to detect damage to or wear of the ball bearing 22 and the roller bearing 23.

In the present embodiment, the output from the one generator part may be converted based on the first threshold value in the first waveform shaping section 91, the output from the other generator part may be converted based on the second threshold value in the second waveform shaping section 94, and the rectangular waves resulting from the conversions may be compared to perform detection.

(Corresponding Relation Between Configuration of the Present Invention and Configuration of the Present Embodiment)

The coil 51a corresponds to one example of a first coil in the present invention, and the iron core (corresponding to 122a in FIG. 8) around which the coil 51a is wound corresponds to one example of a first magnetic pole piece in the present invention.

The coil 51b corresponds to one example of a second coil in the present invention, and the iron core (corresponding to 122b in FIG. 8) around which the coil 51b is wound corresponds to one example of a second magnetic pole piece in the present invention.

Third Embodiment

Next, a third embodiment according to the present invention will be described.

In the description below, only respects different from the first embodiment will be described.

The present embodiment differs from the first embodiment in the configuration of the BPG 9.

Figure 11:
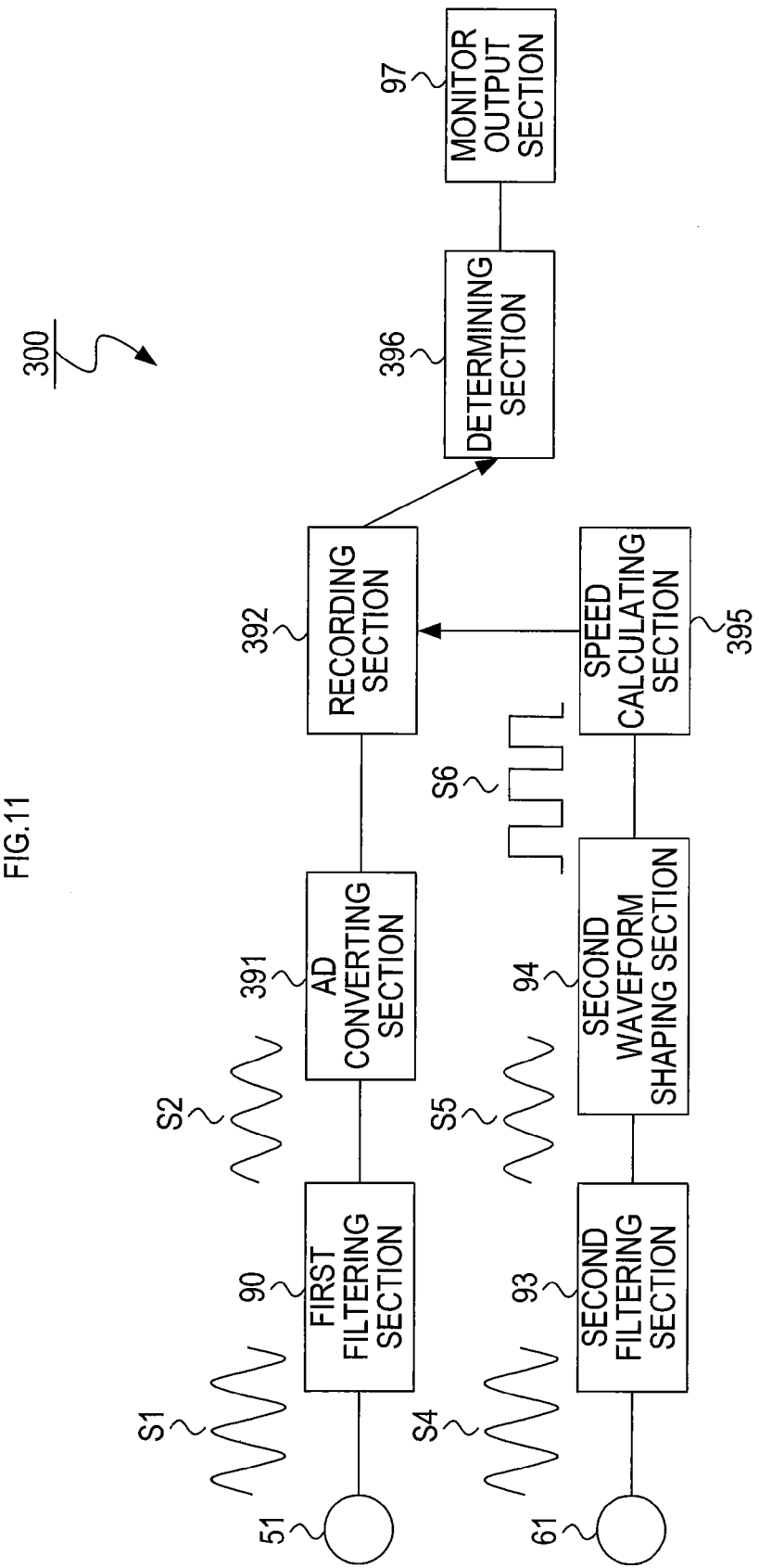
FIG. 11 is a block diagram of a BPG according to a third embodiment.

Specifically, as shown in FIG. 11, the BPG 9 according to the present embodiment comprises: an AD converting section 391 instead of the first waveform shaping section 91 in the first embodiments; a recording section 392 instead of the first speed calculating section 92 in the first embodiment; and a speed calculating section 395 instead of the second speed calculating section 95 in the first embodiment. Additionally, the BPG 9 according to the present embodiment comprises a determining section 396 instead of the speed comparing section 96 in the first embodiment.

The AD converting section 391 performs AD conversion to the signal input from the first filtering section 90, and outputs the AD converted signal to the recording section 392. The speed calculating section 395 detects the speed of a train car based on the signal input from the second waveform shaping section 94, and outputs the detection result to the recording section 392.

The recording section 392 is a device that records, in association with time, a voltage output from the coil 51 and the speed of the train car calculated by the speed calculating section 395.

In the present embodiment, the recording section 392 performs the process of storing a record of output voltages in association with time when the speed of the train car calculated by the speed calculating section 395 is equal to or higher than a certain speed. For example, it performs the process of storing the output voltages when the speed of the train car is equal to or higher than the speed value "a" shown in FIG. 3.

When the voltage output from the coil 51, recorded by the recording section 392, is equal to or smaller than the first threshold value, the determining section 396 determines that the supporting device, such as the ball bearing 22 or the roller bearing 23 is damaged or worn.

Thus, checking voltages output from the coil 51, recorded in a time series, makes it possible to check the process of damage to or wear of the supporting device such as the ball bearing 22 or the roller bearing 23. Additionally, checking whether the output voltage is equal to or smaller than a threshold value or not makes it possible to immediately check whether the supporting device is damaged.

The result of the determination is displayed by use of the monitor outputting section 397 or the like to provide warning to the driver's cab or elsewhere.

The speed may be detected by a separately-provided speed detecting device of the train car, or any other method.

(Corresponding Relation between Configuration of the Present Invention and Configuration of the Present Embodiment)

A description of the corresponding relations between terms will now be given.

The inductor 50 corresponds to one example of an inductor in the present invention, the iron core 52 corresponds to one example of a magnetic pole piece, and the coil 51 corresponds to one example of a coil.

The speed calculating section 395 corresponds to a speed detecting section in the present invention.

The present invention may fall within the spirit of the invention described in the appended claims, and is not limited to the foregoing embodiments.

The invention claimed is:

1. A damage detecting device that detects damage to a supporting device rotatably supporting an armature shaft of an electric motor, the device comprising:
a first speed generator; and
a second speed generator;
wherein the first speed generator comprises:
a disk-shaped first inductor attached to the armature shaft, and having recesses and projections formed at equal pitches along a circumference around a same central axis as the armature shaft;
at least one pair of first magnetic pole pieces, one end of each of the first magnetic pole pieces being joined to one of poles of a first permanent magnet, and the other end of each of the first magnetic pole pieces being disposed opposite the recesses and projections of the first inductor; and
a first coil that detects a change in a magnetic flux passing through the first magnetic pole pieces and generates an output voltage of a waveform corresponding to this detection; and
wherein the second speed generator comprises:
a disk-shaped second inductor attached to an axle of a driving wheel shaft to which power from the electric motor is transmitted via the armature shaft, and having recesses and projections formed at equal pitches along a circumference around a same central axis as the axle;
at least one pair of second magnetic pole pieces, one end of each of the second magnetic pole pieces being joined to one of poles of a second permanent magnet, and the other end of each of the second magnetic pole pieces being disposed opposite the recesses and projections of the second inductor; and
a second coil that detects a change in a magnetic flux passing through the second magnetic pole pieces and generates an output voltage of a waveform corresponding to this detection;
the device further comprising:
a first waveform shaping section that converts the output voltage, generated in the first coil, into a first rectangular wave based on a preset first threshold value;
a second waveform shaping section that shapes the output voltage, generated in the second coil, into a second rectangular wave based on a preset second threshold value; and
a determining section that compares the second rectangular wave and the first rectangular wave and determines, if the first rectangular wave is not output while the second rectangular wave is output, that the supporting device is damaged or worn.

2. A damage detecting device that detects damage to a supporting device rotatably supporting an armature shaft of an electric motor, the device comprising a speed generator, wherein the speed generator comprises:
a disk-shaped inductor attached to the armature shaft, and having recesses and projections formed at equal pitches along a circumference around a same central axis as the armature shaft;
at least one pair of first magnetic pole pieces, one end of each of the first magnetic pole pieces being joined to one of poles of a first permanent magnet, and the other end of each of the first magnetic pole pieces being disposed opposite the recesses and projections of the inductor;
a first coil that detects a change in a magnetic flux passing through the first magnetic pole pieces and generates an output voltage of a waveform corresponding to this detection;
at least one pair of second magnetic pole pieces, one end of each of the second magnetic pole pieces being joined to one of poles of a second permanent magnet, and the other end of each of the second magnetic pole pieces being disposed opposite the recesses and projections of the inductor; and
a second coil that detects a change in a magnetic flux passing through the second magnetic pole pieces and generates an output voltage of a waveform corresponding to this detection;
the device further comprising:
a first waveform shaping section that converts the output voltage, generated in the first coil, into a first rectangular wave based on a preset first threshold value;
a second waveform shaping section that shapes the output voltage, generated in the second coil, into a second rectangular wave based on a preset second threshold value; and
a determining section that compares the second rectangular wave and the first rectangular wave and determines, if the first rectangular wave is not output while the second rectangular wave is output, that the supporting device is damaged or worn.

3. The damage detecting device according to claim 1, wherein the determining section compares the second rectangular wave and the first rectangular wave and, if a duration for which the first rectangular wave is not output while the second rectangular wave is output continues for a predetermined duration, determines that the supporting device is damaged or worn.

4. The damage detecting device according to claim 1, wherein the determining section compares a speed calculated from the first rectangular wave and a speed calculated from the second rectangular wave and, if the speed difference is equal to or larger than a predetermined speed difference, determines that the supporting device is damaged or worn.

5. The damage detecting device according to claim 1, wherein the first threshold value is higher than the second threshold value.

6. A damage detecting device that detects damage to a supporting device rotatably supporting an armature shaft of an electric motor, the device comprising a speed generator, wherein the speed generator comprises:
a disk-shaped inductor attached to the armature shaft, and having recesses and projections formed at equal pitches along a circumference around a same central axis as the armature shaft;
at least one pair of magnetic pole pieces, one end of each of the magnetic pole pieces being joined to one of poles of a permanent magnet, and the other end of each of the magnetic pole pieces being disposed opposite the recesses and projections of the inductor; and a coil that detects a change in a magnetic flux passing through the magnetic pole pieces and generates an output voltage of a waveform corresponding to this detection;

the device further comprising:

a recording section that records, in a time series, the output voltage from the coil; and a determining section that determines that, if the output voltage recorded by the recording section is equal to or smaller than a predetermined threshold value, the supporting device is damaged or worn.

7. The damage detecting device according to claim 6, comprising a speed detecting section that detects speed of a train running by receiving power from the electric motor, wherein the recording section records the output voltage when the speed detected by the speed detecting section is equal to or higher than a certain speed.

8. The damage detecting device according to claim 7, wherein the recording section records the speed detected by the speed detecting section, together with the output voltage.

9. The damage detecting device according to claim 2, wherein the determining section compares the second rectangular wave and the first rectangular wave and, if a duration for which the first rectangular wave is not output while the second rectangular wave is output continues for a predetermined duration, determines that the supporting device is damaged or worn.

10. The damage detecting device according to claim 2, wherein the determining section compares a speed calculated from the first rectangular wave and a speed calculated from the second rectangular wave and, if the speed difference is equal to or larger than a predetermined speed difference, determines that the supporting device is damaged or worn.

11. The damage detecting device according to claim 2, wherein the first threshold value is higher than the second threshold value.

* * * * *